United States Patent
Babaev et al.

(10) Patent No.: US 8,277,472 B2
(45) Date of Patent: Oct. 2, 2012

(54) DEFLECTOR SHIELD FOR USE WITH MULTIPLE WOUND CARE DEVICES

(76) Inventors: Eilaz Babaev, Minnetonka, MN (US); Menendez Adolfo, Woodbury, MN (US)

(*) Notice: Subject to any disclaimer, the term of this patent is extended or adjusted under 35 U.S.C. 154(b) by 0 days.

(21) Appl. No.: 12/199,827

(22) Filed: Aug. 28, 2008

(65) Prior Publication Data

US 2009/0216179 A1  Aug. 27, 2009

Related U.S. Application Data (63) Continuation-in-part of application No. 11/857,162, filed on Sep. 18, 2007, now Pat. No. 7,785,278, and a continuation-in-part of application No. 11/959,577, filed on Dec. 19, 2007, now Pat. No. 7,896,855, and a continuation-in-part of application No. 11/250,870, filed on Oct. 13, 2005, now Pat. No. 7,572,268.

(51) Int. Cl.
  *A61B 17/32* (2006.01)
  *A61B 8/00* (2006.01)
  *A61M 31/00* (2006.01)

(52) U.S. Cl. .................. 606/169; 600/437; 604/500

(58) Field of Classification Search .................. 604/22, 604/500; 606/169; 600/437, 459; 128/200.16
See application file for complete search history.

(56) References Cited

U.S. PATENT DOCUMENTS

| | | | | |
|---|---|---|---|---|
| 4,692,139 | A | * | 9/1987 | Stiles ............................ 604/22 |
| 6,104,952 | A | * | 8/2000 | Tu et al. ........................ 604/20 |
| 2002/0138036 | A1 | * | 9/2002 | Babaev .......................... 604/22 |
| 2004/0186384 | A1 | * | 9/2004 | Babaev ......................... 600/489 |

\* cited by examiner

*Primary Examiner* — Nicholas Lucchesi
*Assistant Examiner* — Rebecca E Eisenberg (57) ABSTRACT

This invention discloses deflector shields to protect an operator from splashing from the use of hand-held ultrasound wound care devices. The deflector shield is for use with an ultrasound generator, ultrasound tip with a radiation surface and a fluid to serve as a coupling medium between the radiation surface and wound surface. The deflector shield is used to protect the operator from splashing fluid and removed tissue. The deflector shield consists of a hub portion and conical portion. The deflector shield is preferably transparent, disposable and easily installed. The deflector shield is preferably useable on several hand-held ultrasound wound care devices.

8 Claims, 9 Drawing Sheets

DEFLECTOR SHIELD FOR USE WITH MULTIPLE WOUND CARE DEVICES

CROSS REFERENCE TO RELATED APPLICATIONS

This application is a continuation-in-part of U.S. patent application Ser. No. 11/857,162 filed Sep. 18, 2007, which claims the benefit of Ser. No. 11/449,220 filed Jun. 7, 2006, the teachings of which are hereby incorporated by reference.

This application is a continuation-in-part of U.S. patent application Ser. No. 11/959,577 filed Dec. 17, 2007 which claims the benefit of Ser. Nos. 11/77,986 and 11/777,990 both filed Jul. 13, 2007, the teachings of which are hereby incorporated by reference.

This application is a continuation-in-part of U.S. patent application Ser. No. 11/250,870 filed Oct. 13, 2005 the teachings of which are hereby incorporated by reference.

BACKGROUND OF THE INVENTION

This invention relates generally to ultrasound point-of-care, such as wound care devices, and, more particularly, to deflector shields to protect an operator from splashing from hand-held debridement devices.

Debridement is the surgical excision of dead, devitalized, and contaminated tissue, and/or the removal of foreign matter from a wound. Hand-held ultrasound wound debridement devices provide a viable option for wound debridement. Hand-held ultrasound wound debridement devices, generally include a fluid system with an ultrasound system to provide and energize a stream of fluid to dislodge unwanted tissue and foreign matter from a wound and may also include a suction system to collect dislodged matter and the irrigated fluid. However, due to the use of a pressurized solution and the ultrasound energy input, the use of such systems can, disadvantageously, result in the splashing of irrigation fluid, tissues, body fluids and debris from the patient onto, e.g, the health care professional operating the irrigation device increasing risks of disease transmission.

Developments have been made to reduce the amount of splash generated from wound debridement devices utilizing a fluid as the mechanism for debridement. Various shields or splash guards have been utilized in an effort to contain and deflect excess irrigation and body fluids away from the health care professional operating the debridement device. Examples of splash shield devices in the prior art include; U.S. Pat. No. 5,441,174 to Sperry, U.S. Pat. No. 6,156,004 to Tremaine et al., US Application No. 2003/0204200 to Rufener, U.S. Pat. No. 6,402,724 to Smith et al. and U.S. Pat. No. 6,293,929 to Smith et al.

Conventional splash deflection devices generally comprise structures formed about and extending outwardly from a debridement tip. These prior art devices suffer from numerous deficiencies. For example, the suction created by the debridement tip typically forms a sufficient vacuum to cause conventional splash deflection shields to adhere to the patient during the debridement procedure, resulting in ineffective irrigation of the wound and discomfort to the patient.

Conventional shield, or deflection devices, due to their materials of construction and their size and shape, often interfere with the user's ability to monitor the area being debrided. Additionally, conventional deflection devices are typically incorporated into a debridement tip and are not capable of being retrofitted to alternative wound debridement devices.

SUMMARY OF THE INVENTION

The present invention includes a splash deflector shield for use with a variety of hand-held ultrasound point-of-care, such as wound care devices. The splash deflector is used to deflect fluid sprayed from the device as well as tissue and other contaminants removed from the wound, away from the operator, more specifically, the operators hand, rather than as a containment device used to contain the aerosolization and splatter as is typical with a number of prior art devices. This use is apparent from the nature and size of the radius of the shield since a deflector has a larger radius and chord length at the distal end while the containment device has a smaller radius and a chord length of approximately the radius at the distal end.

The deflector shield is used in cooperation with a number of prior art devices utilizing ultrasound and a fluid spray, including a cryogenic fluid to improve the usability of the prior art devices in certain applications. The deflector shield is capable of being used on point-of-care, such as wound care and wound debridement devices. Materials of construction may be selected so that it can be economically disposed of after each use. The deflector shield may be formed from optically clear materials to provide a deflector shield through which the treated area may be viewed during the medical procedure.

The deflector shield is effective at controlling spray back-splash from the wound, yet does not have a tendency to adhere itself to the patient undergoing debridement.

The deflector shield acts more as a deflector, i.e. to deflect away from the operator, more specifically, the operators hand, rather than as a containment device i.e. to contain the aerosolization and splatter.

The deflector shield may be provided of optically clear materials to prevent visual obstruction of the application or procedure being accomplished.

The deflector shield may be flexible and soft to the touch to prevent irritation of the application or procedure site and/or its periphery and when necessary to conform to the site topography.

The deflector shield has sufficient inherent structural integrity to not droop or sag under its own weight and flexibility and yet not deform after fabrication or molding or in its packaging from storage or transportation.

The deflector shield mounts in a user-friendly fashion, is easy to use, remove or discard, and provides tactile feedback to the operator to ensure it is properly mounted and securely in position.

The present invention comprises a transparent shield having a substantially central aperture sized to accommodate an ultrasound tip. With an ultrasound tip traversing the central aperture of the shield of the present invention, the shield is operable to decrease splash generated during use of a debridement device, while not being susceptible to vacuum adhering to the subject patient.

Advantageously, the splash deflection shield of the present invention is adapted to be retrofit to both newly manufactured and pre-existing wound debridement devices, and may be used with debridement tips having various configurations and spray patterns. Because the shield of the present invention may be used with such a variety of debridement devices, it is economical and convenient to use.

The present invention may provide a splash deflection shield which effectively deflects splash away from the operator and which does not adhere to the patient during use.

The present invention may provide a splash deflection shield adapted to be retrofit to various pre-existing wound debridement and other point-of-care devices.

The present invention may provide a splash deflection shield for use with a debridement device which does not interfere with, or distort, the operator's view of the area being debrided.

BRIEF DESCRIPTION OF THE DRAWINGS

The aforementioned and other features and objects of this invention, and the manner of attaining them, will become apparent and the invention itself will be better understood by reference to the following description of an embodiment of the invention taken in conjunction with the accompanying drawings, wherein.

DETAILED DESCRIPTION OF THE INVENTION

Figure 1:
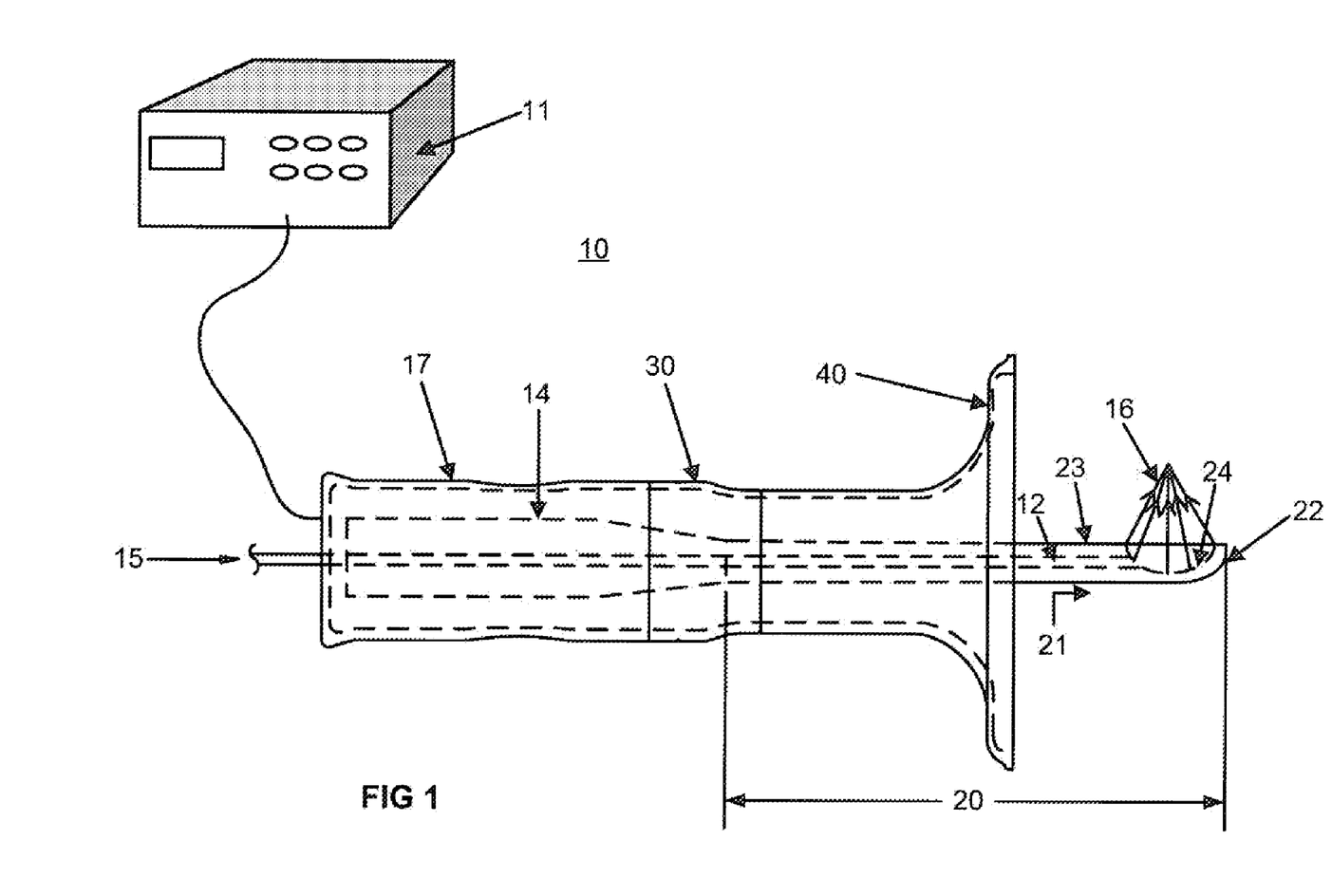
FIG. 1 is a perspective view of the present invention with a radial orientation of the radiation surface.

One embodiment of the deflector shield 40 is shown in use in FIG. 1 as an element of device 10. The device 10 consists of an ultrasound generator 11 producing a signal to drive an ultrasound transducer 14. The ultrasound transducer 14 produces ultrasound waves and is attached to an ultrasound tip 20 to transmit the ultrasound energy to a distal end 21.

The ultrasound transducer may be covered with a housing 17 to isolate the operator's hand from the transducer. The housing 17 may extend over the ultrasound tip 20.

The ultrasound tip 20 may have an interior passage 12 to deliver fluid 15 to the distal end 21. The fluid may serve as a coupling medium 16 to transmit ultrasound waves from the ultrasound tip 20 to a wound surface.

The ultrasound energy and fluid 15 may be discharged from a radiation surface 24 located on the radial surface 23 of the distal end 21 of the ultrasound tip 20. The radiation surface 24 may be in the form of a parabolic chamber or spoon shape on the radial surface 23. The use of a device without the deflector shield 40 is described in U.S. patent application Ser. No. 11/857,162 filed Sep. 18, 2007 which is incorporated by reference in its entirety.

As shown in FIG. 1, the housing 17 may be attached to a deflector shield 40 that covers portions of the ultrasound tip 20. The deflector shield may optionally be attached to the housing 17 through a shield adapter 30 that surrounds the tip as a ring. The deflector shield 40 and the shield adapter 30 are preferably physically isolated from the tip to reduce the transmission of vibrations to the housing 17.

Figure 2:
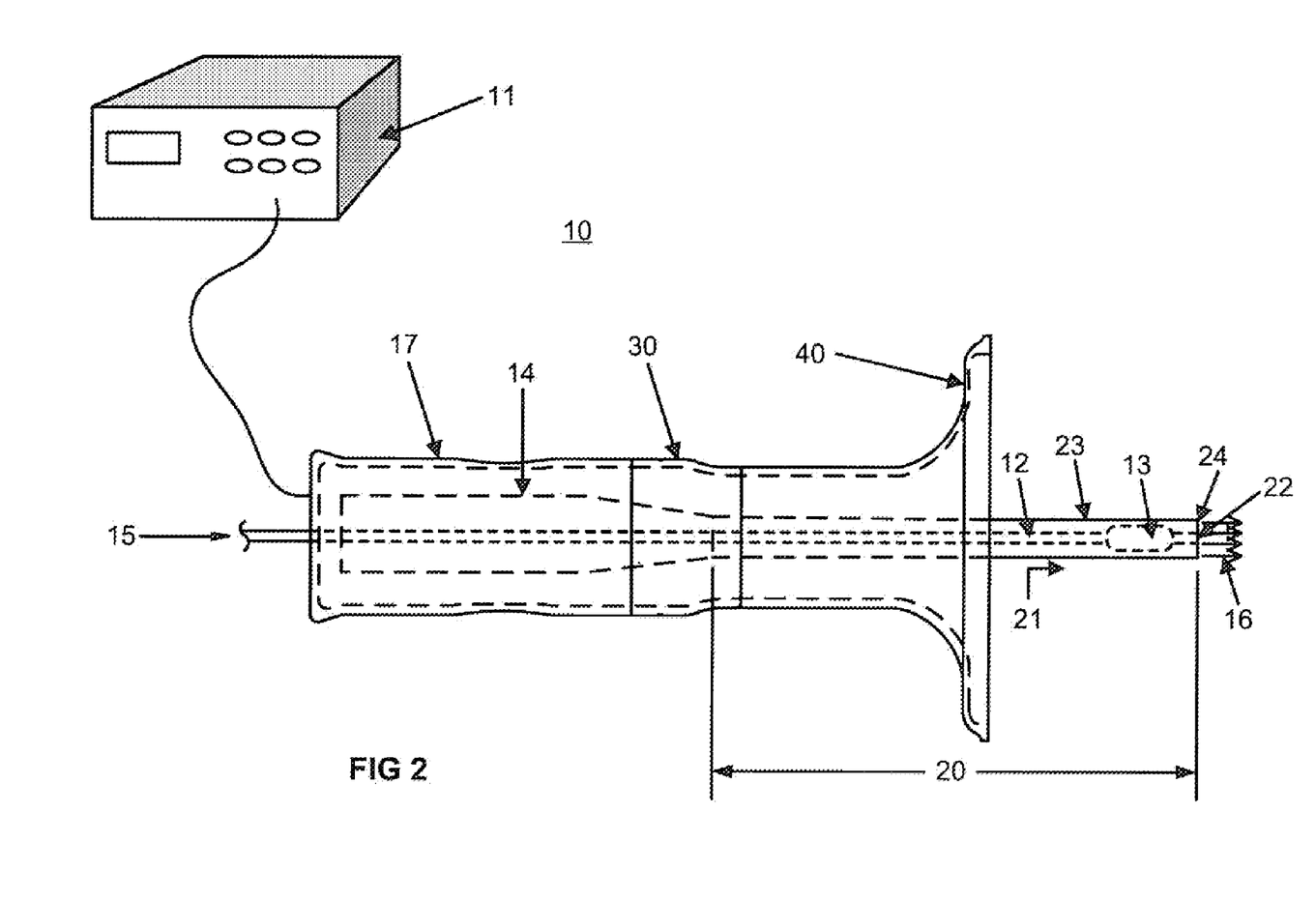
FIG. 2 is a perspective view of the present invention with a longitudinal orientation of the radiation surface.

FIG. 2 discloses an alternative embodiment of the device 10 shown in FIG. 1 in which the ultrasound energy is being transmitted through a distal surface 22. In this embodiment, ultrasound waves are emitted with from the radiation surface 24 with a longitudinal orientation parallel to the axial centerline of the ultrasound tip 20. The fluid 15, used as a coupling medium 16 is directed to the wound using a radiation surface 24 with a defined shape on the distal surface 24. In some embodiments, the ultrasound tip 20 may contain a portion of the interior passage 12 as a chamber 13 to allow mixing, activation and/or additional holding time of the fluid within the ultrasound tip 20. Various embodiments of the radiation surface 24, the ultrasound tip 20 and methods for using and focusing the ultrasound radiation are described in U.S. patent application Ser. No. 11/959,577 filed Dec. 17, 2007 the teachings of which are hereby incorporated by reference in its entirety.

The use of a device and various embodiments for using and focusing the ultrasound radiation in a device for the cryogenic ablation of tissue without the deflector shield 40 are described in U.S. patent application Ser. No. 11/250,870 filed Oct. 13, 2005 the teachings of which are hereby incorporated by reference in its entirety.

Figure 3:
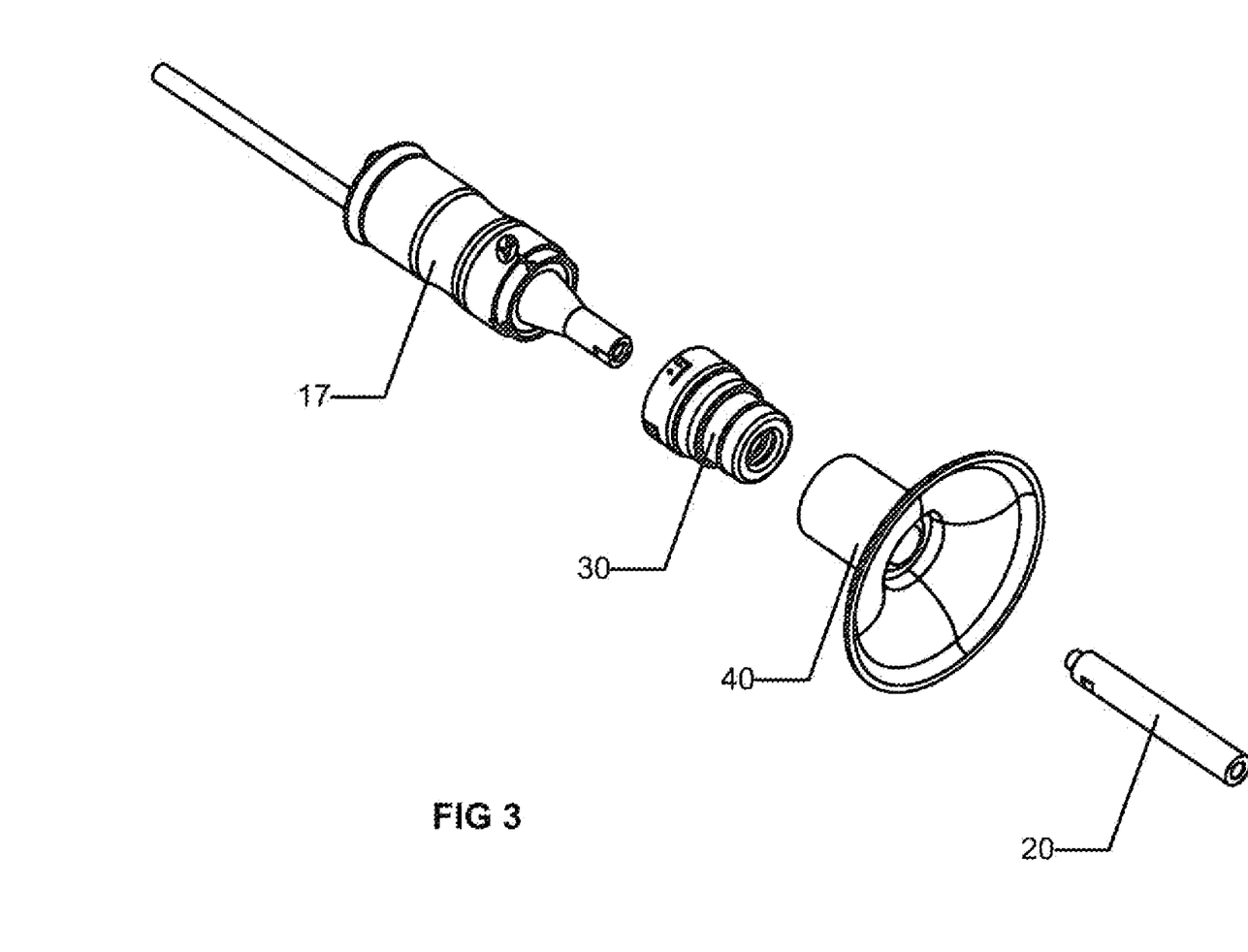
FIG. 3 is an exploded view of the present invention with a longitudinal orientation of the radiation surface.

An exploded view of the hand-piece of an embodiment of the invention is shown in FIG. 3. Optionally, the shield adapter 30 is used to cover portions of the ultrasound tip 20 and may be used to position the deflector shield 40. The shield adapter 30 is particularly useful when patients are known to have blood or tissue born communicable disease. The shield adapter 30 may attach to the housing 17 through mechanical means such as for example, an O-ring, threaded connection or mechanical tabs. The deflector 40 shield may attach to the shield adapter 30 through alternative mechanical means, examples of which may include an O-ring, threading or mechanical tabs.

Figure 4:
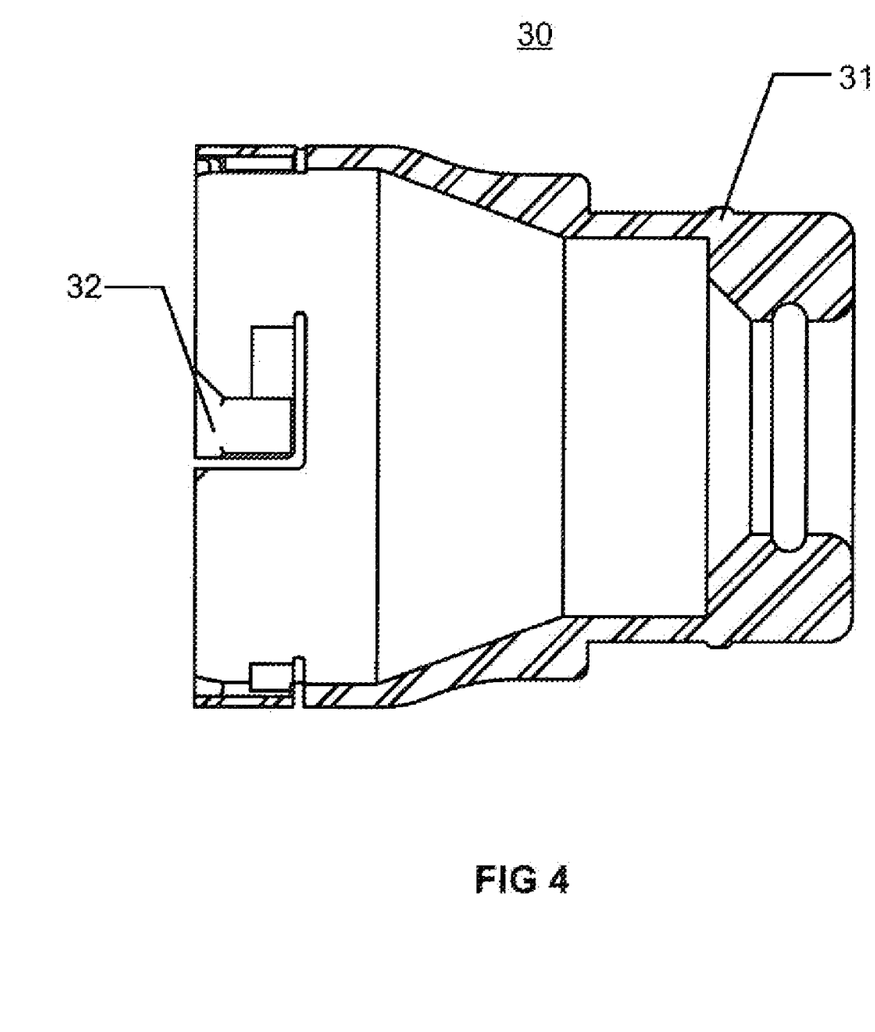
FIG. 4 is an elevational view of an embodiment of the shield adapter.

One embodiment of the removable shield adapter 30 is shown in FIG. 4. The shield adapter allows easy installation of alternative shield configurations. To create a press fit the shield adapter 30 may have a protruding ring 31 slightly raised from the exterior surface of the shield adapter 30 to interlock with the deflector shield 40 and a mechanical attachment tab 32 or threaded connection for attachment to the housing 17. The shield adapter 30 is preferably of a generally open cylindrical shape to provide isolation from the ultrasound tip 20.

Figure 5:
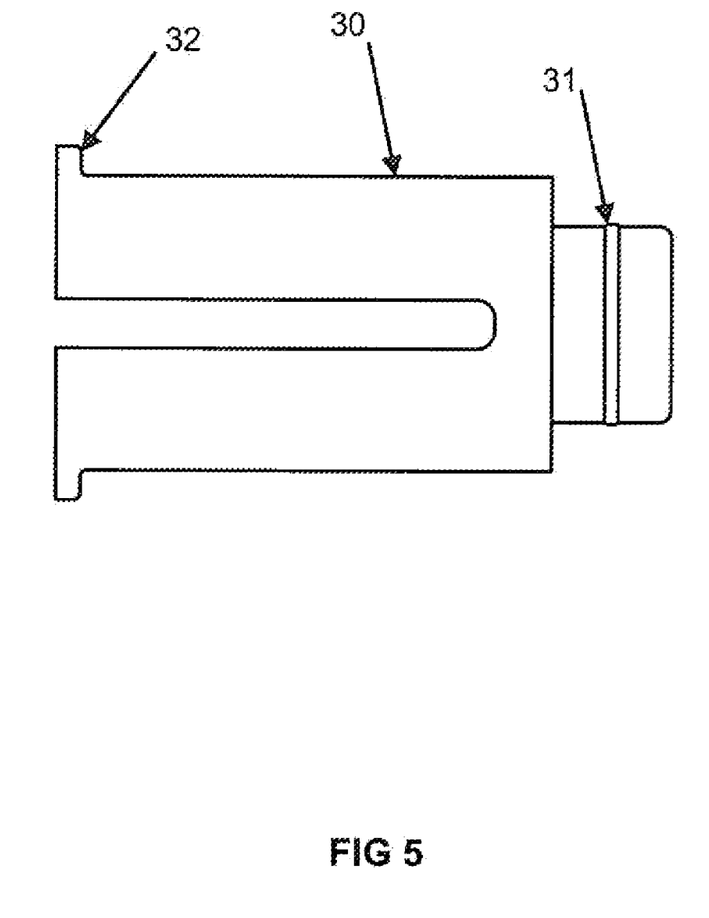
FIG. 5 is an elevational view of an alternative embodiment of the shield adapter.

FIG. 5 is an elevational view of an alternative embodiment of the shield adapter 30 showing its use as an extension piece with an alternative mechanical attachment tab 32.

A hand piece may be used with or without a deflector shield 40. The deflector shield 40 is preferably a disposable unit and therefore preferably constructed of a plastic material that generally maintains its shape during use, but exhibits sufficient flexibility in use to allow deformation when necessary for manipulation of the hand piece next to the patients skin without causing discomfort to the patient. Typical materials of use include; pvc, polyethylene or teflon. A silicone elastomer is preferred because of its optical clarity, mechanical characteristics and its low cost allow its economical use as a single-use item. When a deflector shield 40 is used, the deflector shield 40 may be directly coupled to the ultrasound tip 20 or it may be isolated from the ultrasound tip and directly coupled to the housing 17, or it may be directly coupled to the shield adapter 30.

Figure 6:
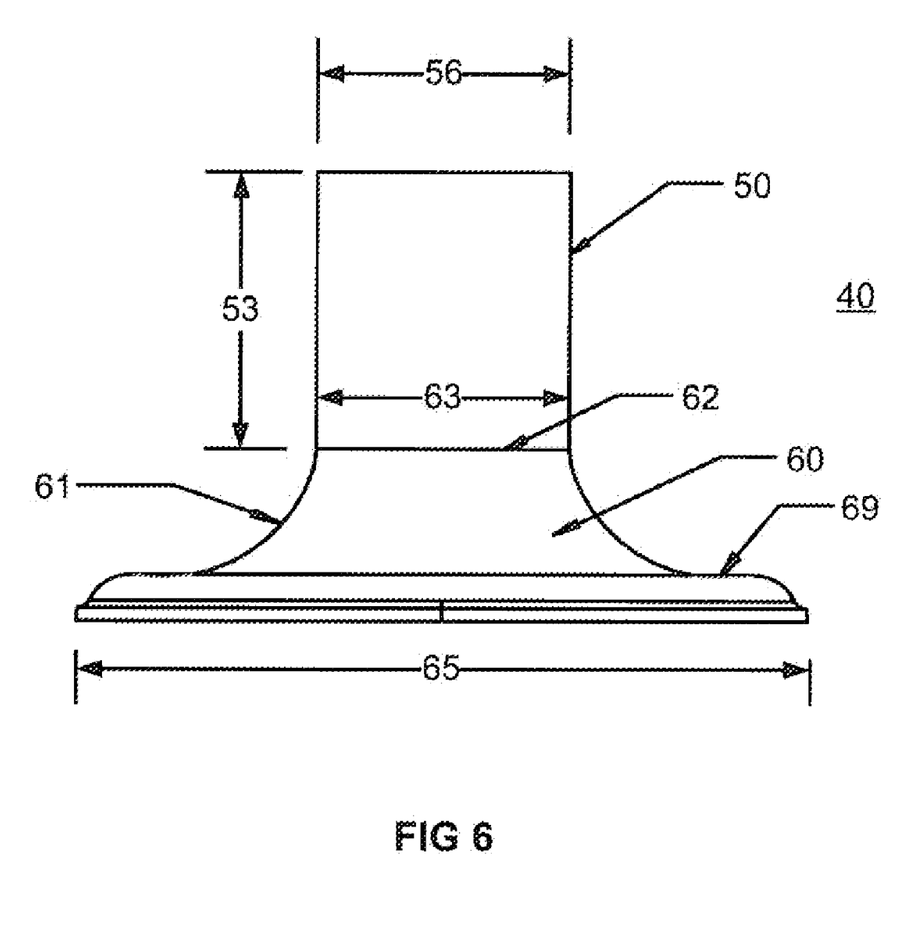
FIG. 6 is an elevational view of an embodiment of the deflector shield.

An embodiment of the deflector shield 40 is shown in FIG. 6. The deflector shield 40 may include a hub portion 50 located at the proximal end of the deflector shield 40 and a conical portion 60 located at the distal end of the deflector shield 40

The hub portion 50 may be preferably a hollow cylindrical surface with a length 53 and an outer diameter 56.

A conical portion 60 is located at the deflector shield 40 distal end. The conical portion 60 is preferably frusto conical with the profile of an outer surface being a concave surface 61. The conical portion 60 has an upper base 62 with an upper diameter 63 adjacent the hub portion 50. The upper diameter 63 is preferably approximately equivalent to the hub diameter 56. The conical portion 60 distal end preferably has an elliptical or circular outline with a lower diameter 65 and may include a raised lip 69 that includes a ribbed edge to provide structural strength with minimal increased material and weight.

Figure 7:
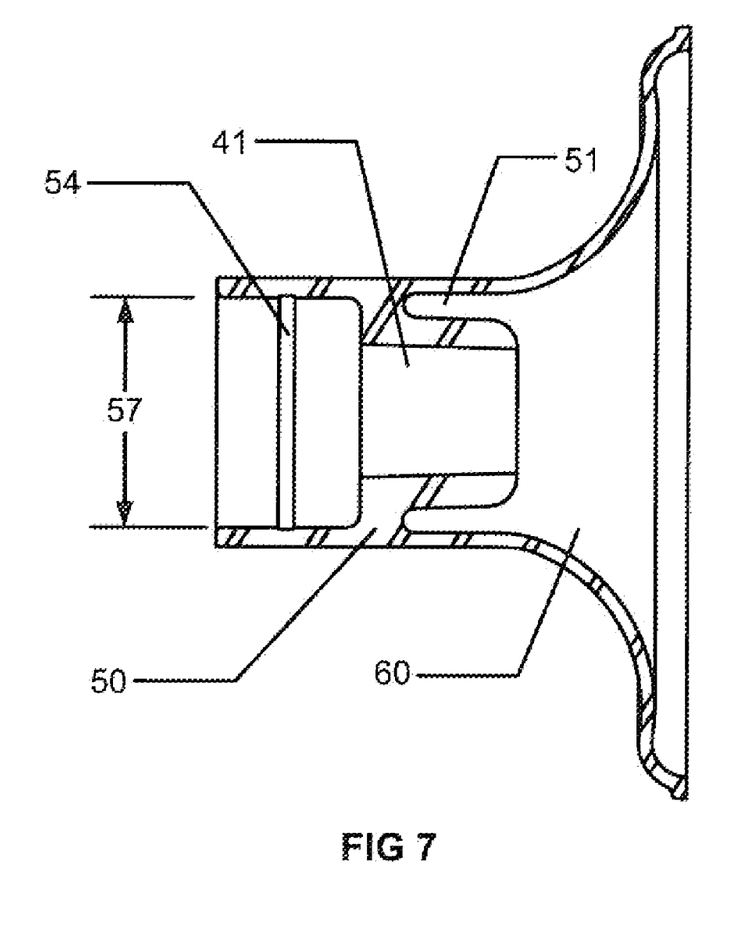
FIG. 7 is a cross-sectional view of an embodiment of the deflector shield.

FIG. 7 is a cross-sectional view of an embodiment of the deflector shield as shown in FIG. 6. A central aperture 41 is sized to at least contain the ultrasound tip 20. It may also be provided with adequate clearance to prevent direct contact with the ultrasound tip 20. The deflector shield 40 may contain a receiving cavity 51 located near the interface between the hub portion 50 and the conical portion 60. The conical portion 60 extends radially from the central aperture 41. The receiving cavity 51, formed by the protrusion of the hub portion 50 into the conical portion 60 provides improved performance of the deflector shield 40 by enhancing capture of sprayed fluids and reducing backsplash. Furthermore, the receiving cavity 51 prevents contact of the splashing fluid and debris with the vibrating surface of the ultrasound tip 20 radial portion. This of course reduces reatomization of the backsplash fluid from the radial surface.

The cavity also allows channeling of the splashing fluid for effective removal of the collected fluid away from ultrasound tip 20 so that it will not build up and be resuspension or reflection of the fluid back into the air. The receiving cavity 51 also further isolates the conical portion 60 from the ultrasound tip 20. As the device is positioned during use on a patient, the conical portion 60 may deform when contacted against skin surface. The receiving cavity 51 allows the conical portion 60 to deform without contacting the ultrasound tip 20. Even with substantial deformation, the conical portion 60 that exceeds the open space provided in the conical portion 60, the conical portion 60 will contact the hub portion 50 surrounding the ultrasound tip 20 and not contact the ultrasound tip 20 directly. This will prevent excessive unwanted ultrasound energy from being transferred to the patient tissues through the conical portion 60 of the deflector shield 40.

Cylindrical surfaces are optionally provided with a relief of 1.6 degrees to improve manufacturability, assembly and detachment of the deflector shield 40 to the hand piece. The hub may also have a groove 54 located on an inner hub diameter 57 to accept the adapter ring 31 or an O-ring.

Figure 8:
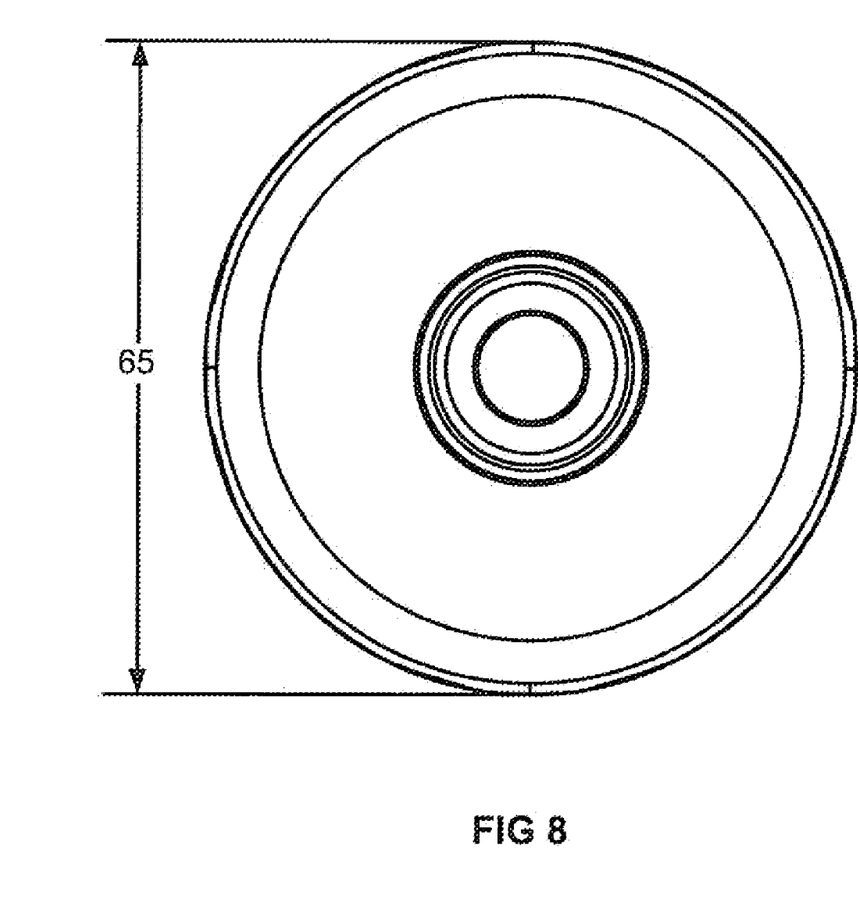
FIG. 8 is a distal end view of an embodiment of the deflector shield.

FIG. 8 is a distal end view of an embodiment of the deflector shield showing a circular embodiment with a lower diameter 65.

Figure 9:
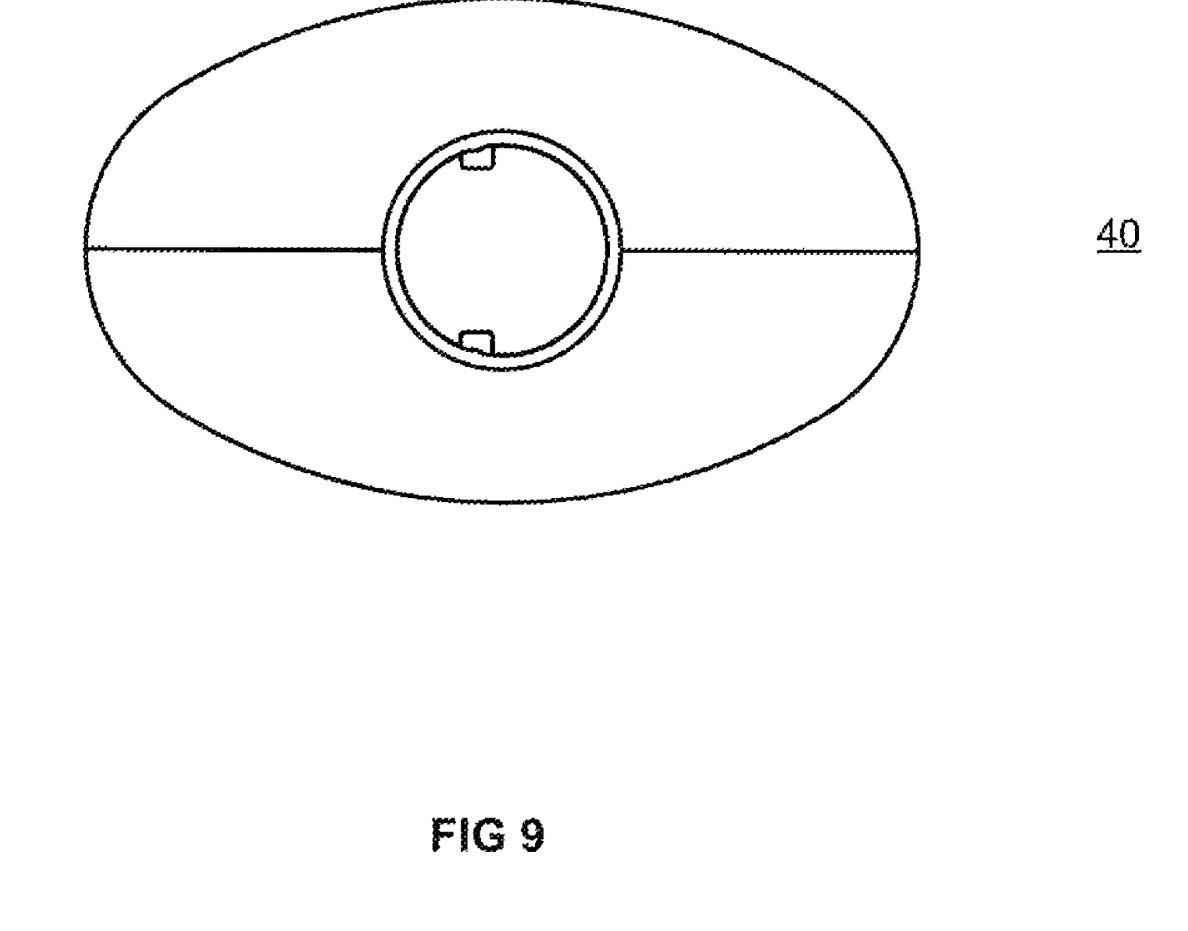
FIG. 9 is a distal end view of an embodiment of the deflector shield.

FIG. 9 is a distal end view of an embodiment of the deflector shield 40 in an elliptical embodiment with a mechanical tab or snap coupling feature embodiment.

Under the preferred embodiment, the deflector shield 40 may have the following dimensions.

Conical Portion Lower Diameter: approximately 3.4 inches
Hub Outer Diameter: approximately 1.2 inches
Hub Length: approximately 1.3 inches
Material: Elastomer (Silicone)
Finish: Optically Clear
Durometer (Hardness): 48-57 (Shore 50A—Medium Soft)

The embodiment disclosed is not intended to be exhaustive or to limit the invention to the precise form disclosed in the detailed description. Rather, the embodiments are chosen and described such that others skilled in the art might utilize their teachings.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which the invention pertains.

What is claimed is:

1. An ultrasound wound care device comprising:
    a. an ultrasound generator driving an ultrasound transducer to produce ultrasound waves;
    b. an ultrasound tip attached to the ultrasound transducer;
    c. the ultrasound tip directing the ultrasound waves to a radiation surface at the distal end of the ultrasound tip;
    d. an interior passage axially disposed within the ultrasound tip;
    e. a fluid passing through the interior passage, the fluid discharged from a distal surface of the ultrasound tip with the ultrasound waves;
    f. a deflector shield axially disposed around a portion of the ultrasound tip comprising;
        i. a hub portion including a central aperture sized to accommodate the ultrasound tip;
        ii. the hub portion attached to a conical portion;
        iii. the conical portion extending radially from the central aperture; and
        iv. a receiving cavity located concentrically between the hub portion and the conical portion;
        v. wherein the said conical portion radiates outwards from a smaller proximal end located at a distal end of said cavity to a wider distal end; and
        vi. wherein the hub potion of the deflector shield projects into the conical portion of said shield and the receiving cavity being formed by the protrusion of the hub portion into the conical portion.

2. The device of claim 1 also having a chamber within the ultrasound tip, the chamber in fluid communication with the interior passage.

3. The device of claim 1 also having the radiation surface forming a parabolic cavity.

4. The device of claim 1 wherein the ultrasound tip receives a cryogenic fluid.

5. The device of claim 1 wherein the fluid serves as a coupling medium to transport the ultrasound waves.

6. The device of claim 1 wherein the fluid serves as a coupling medium to transport the ultrasound waves.

7. The device of claim 1 wherein the fluid serves to irrigate a wound.

8. A method of administering wound care comprising the steps of:
    a. providing a wound care device comprising:
        i. an ultrasound generator driving an ultrasound transducer to produce ultrasound waves;
        ii. an ultrasound tip attached to the ultrasound transducer;
        iii. the ultrasound tip directing the ultrasound waves to a radiation surface at the distal end of the ultrasound tip;
        iv. an interior passage axially disposed within the ultrasound tip;
        v. a fluid passing through the interior passage, the fluid discharged from a distal surface of the ultrasound tip with the ultrasound waves;
        vi. a deflector shield axially disposed around a portion of the ultrasound tip comprising:
            1. a hub portion including a central aperture sized to accommodate the ultrasound tip;

2. the hub portion attached to a conical portion;
3. the conical portion extending radially from the central aperture; and
4. a receiving cavity located concentrically between the hub portion and the conical portion;
5. wherein the said conical portion radiates outwards from a smaller proximal end located at a distal end of said cavity to a wider distal end; and
6. wherein the hub potion of the deflector shield projects into the conical portion of said shield and the receiving cavity being formed by the protrusion of the hub portion into the conical portion;

b. producing the ultrasound waves within the ultrasound tip;
c. directing the ultrasound waves to the radiation surface;
d. directing the fluid to the radiation surface;
e. delivering the ultrasound waves to a wound through the fluid serving as a coupling medium;
f. positioning the deflector shield between an operator and the wound; and
g. treating the wound.

* * * * *